United States Patent [19]
McLeod

[11] Patent Number: 6,053,866
[45] Date of Patent: Apr. 25, 2000

[54] METHOD FOR FACILITATING DIAGNOSIS OF A PSYCHIATRIC DISORDER

[76] Inventor: Malcolm N. McLeod, 419 Lakeshore Dr., Chapel Hill, N.C. 27514

[21] Appl. No.: 09/182,729

[22] Filed: Oct. 29, 1998

[51] Int. Cl.⁷ .................................................. A61B 5/00
[52] U.S. Cl. ........................................ 600/300; 600/545
[58] Field of Search .................................... 600/300, 545

[56] References Cited

U.S. PATENT DOCUMENTS

| | | | |
|---|---|---|---|
| 4,464,122 | 8/1984 | Fuller et al. | 434/262 |
| 4,733,354 | 3/1988 | Potter et al. | 364/415 |
| 5,473,537 | 12/1995 | Glazer et al. | 364/419.2 |
| 5,596,994 | 1/1997 | Bro | 128/732 |
| 5,913,310 | 6/1999 | Brown | 128/897 |
| 5,935,060 | 8/1999 | Iliff | 600/300 |

*Primary Examiner*—Max Hindenburg
*Assistant Examiner*—Brian Szmal
*Attorney, Agent, or Firm*—Jenkins & Wilson, P.A.

[57] ABSTRACT

A method of facilitating diagnosis of a psychiatric disorder in a patient is disclosed. The method includes the steps of providing the patient with one or more questions relating to symptoms of one or more psychiatric disorders in a format which facilitates recording the patient's answers to the one or more questions; and establishing a preliminary disorder indication based on the answers provided by the patient to the one or more questions. The diagnosis of a psychiatric disorder in the patient is thus facilitated by the format which facilitates recording the patient's answers to the one or more questions and by the establishing a preliminary disorder indication.

20 Claims, 1 Drawing Sheet

METHOD FOR FACILITATING DIAGNOSIS OF A PSYCHIATRIC DISORDER

DESCRIPTION

1. Technical Field

The present invention relates generally to a method of recording and processing mental health data from a patient. More particularly, the present invention relates to a method for recording and processing of health and symptom data from a patient for use in facilitating the diagnosis of a psychiatric disorder in the patient.

2. Background Art

It will be appreciated by those of skill in the art that it is difficult to obtain appropriate data from a patient for use in diagnosing a psychiatric disorder in the patient. It is often very difficult for a person who is troubled emotionally or psychiatrically to clearly identify and understand his or her difficulties. It is also difficult to encourage such a person to become involved in decisions affecting his or her health care.

From the perspective of a healthcare provider, the documentation of symptoms associated with major psychiatric disorders, which is part of a thorough psychiatric examination, is a difficult and time-consuming process. Thus, the health care provider must spend more time on documentation and less time on the person and his or her individual difficulties.

It is also difficult to make a thorough diagnosis of a patient because the patient is upset and usually does not have enough time with the health care provider to give a complete and thorough history. A complete and thorough history is very important to an accurate psychiatric diagnosis in that the data in a history is usually all the health care provider has to establish a diagnosis.

Usually, the patient feels rushed, and often actually is rushed, during a session with a health care provider. The health care provider is often overburdened as well, and does not have time to obtain data from the patient and prepare a thorough evaluation of the patient. This is particularly the case in this day and age of managed care programs which structure the amount of time a patient can spend with the health care provider.

The *Diagnostic and Statistical Manual of Mental Disorders, Fourth Edition* (DSM-IV), published by the American Psychiatric Association, has established categories of psychiatric disorders. These categories were formulated by over one thousand mental health professionals and members of numerous professional organizations on the basis of clinical research, field trials and extensive review of the literature. It is the general view of mental health professionals that an evaluation of an emotionally or psychiatrically troubled person is not thorough unless the DSM-IV categories have been carefully considered. However, while the DSM-IV is very thorough and detailed, it is also quite lengthy, having approximately 886 pages. Thus, the process of reviewing the categories and applying them to data from a patient is also very time-consuming and arduous.

What is needed, then, is a method for facilitating the diagnosis of a psychiatric disorder which provides for patient involvement, considers the categories of the DSM-IV, and facilitates the documentation of data concerning the patient's symptoms. Such a method is currently unavailable in the art.

SUMMARY OF THE INVENTION

A method of facilitating diagnosis of a psychiatric disorder in a patient is disclosed. The method comprises the steps of providing the patient with one or more questions relating to symptoms of one or more psychiatric disorders in a format which facilitates recording the patient's answers to the one or more questions; and establishing a preliminary disorder indication based on the answers provided by the patient to the one or more questions. The diagnosis of a psychiatric disorder in the patient is thus facilitated by the format which facilitates recording the patient's answers to the one or more questions and by the establishing of a preliminary disorder indication.

It is an object of the present invention to facilitate a diagnosis of a psychiatric disorder in a patient.

It is another object of the present invention to encourage and empower a patient to participate in the process of diagnosing a psychiatric disorder in the patient.

It is a further object of the present invention to provide an improved method for recording and processing health and symptom data from a patient for use in diagnosing a psychiatric disorder in the patient.

It is yet a further object of the present invention to facilitate a diagnosis of a psychiatric disorder in a patient by providing questions concerning the symptoms of all psychiatric disorders in a format that enables to the patient to answer the questions with no time limit.

It is still a further object of the present invention to facilitate a diagnosis of a psychiatric disorder in a patient by providing questions concerning the symptoms of all psychiatric disorders in a format that enables to the patient to establish a self assessment of a psychiatric condition in the patient.

It is yet another object of the present invention to facilitate a diagnosis of a psychiatric disorder by freeing the health care provider's so that the health care provider can address particular concerns of individual patients.

Some of the objects of the invention having been stated hereinabove, other objects will become evident as the description proceeds, when taken in connection with the accompanying Examples and Drawings as best described hereinbelow.

DETAILED DESCRIPTION OF THE INVENTION

Figure 1:
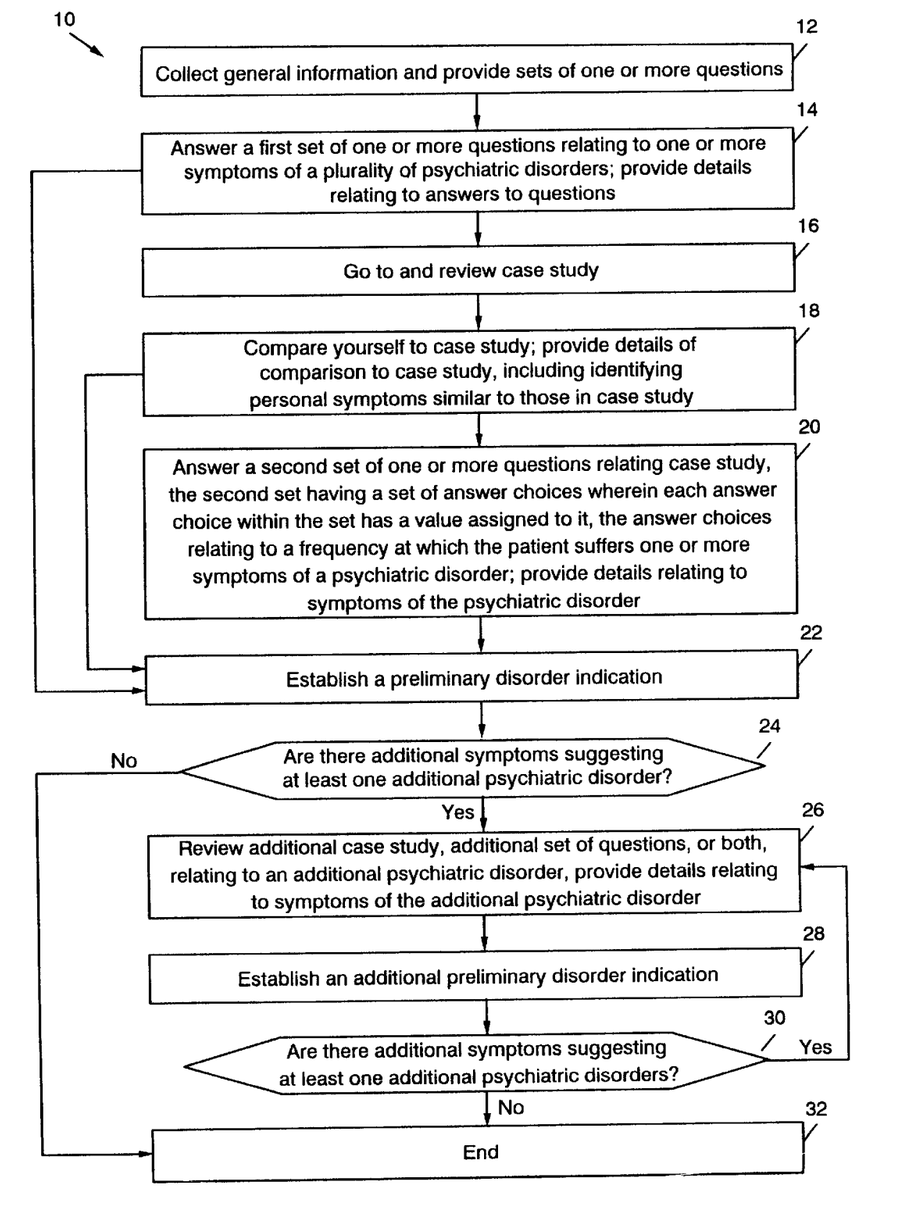
The FIGURE is a block diagram illustrating the method of the present invention.

In accordance with the present invention a method of facilitating diagnosis of a psychiatric disorder in a patient is provided. The method comprises the steps of providing the patient with one or more questions relating to symptoms of one or more psychiatric disorders in a format which facilitates recording the patient's answers to the one or more questions; and establishing a preliminary disorder indication based on the answers provided by the patient to the one or more questions, whereby diagnosis of a psychiatric disorder in the patient is facilitated.

Optionally, the one or more questions have a set of answer choices wherein each answer choice within the set has a value assigned to it, the answer choices relating to a frequency at which the patient suffers the symptoms of a psychiatric disorder. Preferably, the value assigned to each of the answer choices comprises a numerical value. In this case the step of establishing a preliminary disorder indication based on the values of the answer choices chosen by the patient to the one or more questions further comprises summing the numerical values of the answer choices chosen by the patient to the one or more questions; and establishing a preliminary disorder indication based on a sum of the values of the answer choices chosen by the patient to the one or more questions. More preferably, the step of establishing a preliminary disorder indication based on a sum of the values of the answer choices chosen by the patient to the one or more questions further comprises providing a numerical range such that if the sum of the values of the answer choices chosen by the patient to the one or more questions falls within the numerical range, the sum is indicative of a particular preliminary disorder indication.

The diagnosis or diagnoses of a wide variety of psychiatric disorders may be facilitated in accordance with the present invention. Indeed, in a preferred embodiment, the present invention provides questions that relate to symptoms of all psychiatric disorders. More preferably, the psychiatric disorders are selected from a group including, but not limited to, major depressive disorder, dysthymia, manic episode, hypomanic episode, bipolar disorder, alcohol abuse, alcohol dependence, drug abuse, drug dependence, pre-menstrual syndrome, obsessive disorder, compulsive disorder, panic disorder, phobias, generalized anxiety disorder, eating disorder, acute stress disorder, post traumatic stress disorder, dissociative disorders, and combinations thereof. More preferably, the one or more questions relating to one or more symptoms of one or more psychiatric disorders track categories of psychiatric disorders presented in the *Diagnostic and Statistical Manual of Mental Disorders, Fourth Edition.*

The present invention facilitates a diagnosis of a psychiatric disorder in a patient by providing questions concerning the symptoms of all psychiatric disorders in a format that enables to the patient to answer the questions with no time limit. The present invention also facilitates a diagnosis of a psychiatric disorder in a patient by providing the questions in a format that enables to the patient to establish a self assessment of a psychiatric condition in the patient. Thus, the health care provider's time is unburdened, and the health care provider take the time to individualized concerns of the patient.

While the following terms are believed to be well understood by one of skill in the art, the following definitions are set forth to facilitate explanation of the invention.

The term "health care provider" is meant to refer to physicians, family practitioners, psychiatrists, psychologists, psychoanalysts, social workers, nurses or any other professional who provides health care services, particularly health care services.

The terms "general health information" and "general identifying information" are meant to refer to background information on a patient's health, including last visit to a doctor, family history, personal history and similar information and to other personal data from the patient, including name, address, telephone number and similar information.

The term "preliminary disorder indication" is meant to refer to a disorder which a patient may be suffering, as indicated by data produced in accordance with the method of the present invention.

Following long-standing patent law convention, the terms "a" and "an" mean "one or more" when used in this application, including the claims.

Referring now to the FIGURE, wherein like reference numerals refer to like blocks throughout, a block diagram illustrating the method of the present invention is referred to generally at 10. Block diagram 10 includes a series of arrows which connect the blocks in accordance with varied and optional sequences in which one may perform the method of the present invention, the steps of which being embodied by the blocks as described herein below.

Continuing with the FIGURE, block 12 refers to the step of providing the patient with sets (preferably at least two sets) of one or more questions relating to one or more symptoms of a plurality of psychiatric disorders in a format which facilitates recording the patient's answers to the questions. Block 14 refers to the step of directing the patient to answer a first set of one or more questions relating to one or more symptoms of a plurality of psychiatric disorders. Block 14 also refers to the step of directing the patient to provide details relating to the patient's answers to the questions. As indicated by the arrows from box 14 to box 22, a preliminary disorder indication can optionally be established based on the patient's answers to the first set of questions. However, it is generally desirable to obtain additional data from the patient for use in conjunction with the patient's answers to the first set of questions to establish a preliminary disorder indication. Thus, preferably, the method of the present invention as schematically presented in block diagram 10 proceeds from box 14 to box 16.

Continuing with the FIGURE, block 16 refers to the step of directing the patient to a case study describing a psychiatric disorder based on the patient's answers to the first set of one or more questions. Block 18 refers to the step of directing the patient to compare himself or herself to the case study and to provide details of this comparison to case study, including identifying personal symptoms similar to those presented in the case study. As indicated by the arrows from box 18 to box 22, a preliminary disorder indication can optionally be established based on the patient's comparison of himself or herself to the case study. However, it is generally desirable to obtain additional data from the patient for use in conjunction with the patient's comparison of himself or herself to the case study to establish a preliminary disorder indication. Thus, preferably, the method of the present invention as schematically presented in block diagram 10 proceeds from box 18 to box 20.

Continuing with the FIGURE, block 20 refers to the step of directing the patient to answer a second set of one or more questions relating to one or more symptoms of the psychiatric disorder described in the case study. The second set of one or more questions also includes a set of answer choices wherein each answer choice within the set has a value assigned to it. The answer choices relate to the frequency at which the patient suffers the one or more symptoms of the psychiatric disorder described in the case study.

Continuing with the FIGURE, block 22 refers to the step of establishing a preliminary disorder indication based on the values of the answer choices chosen by the patient to the second set of questions. As noted above, the establishing of a preliminary disorder indication also considers the patient's answers to the first set of questions and the patient's comparison of himself or herself to the case study. In accordance with the objects of the present invention, it is preferred the patient establish the preliminary disorder indication himself or herself. Optionally, however, the patient may be assisted in establishing the preliminary disorder indication by a mental health professional.

Continuing with the FIGURE, block 24 inquires of the patient as to whether there are any additional symptoms suggesting an additional psychiatric disorders, based on the patient's answers to the first set of one or more questions, on the patient' response to the case study, or on the patient's answers to the second set of one or more questions. If "Yes", then the method of the present invention proceeds to block 26, which refers to the step of directing the patient either to an additional case study or an additional set of questions, or to both. Thus, the additional case study and the additional set of questions relate to an additional psychiatric disorder. If "No", then the method of the present invention proceeds to "END" block 32, which terminates the method with the respect to the patient.

Continuing with the FIGURE, block 28 refers to the step of establishing an additional preliminary disorder indication based on the answers or responses by the patient to the additional case study, the additional set of questions, or to both. Block 30 inquires of the patient as to whether there are any additional symptoms suggesting an additional psychiatric disorders, based on the patient's answers and responses to the additional case study, to the additional set of questions, or to both. If "Yes", then the method of the present invention proceeds back to block 26, which refers to the step of directing the patient either to an additional case study or an additional set of questions, or to both. If "No", then the method of the present invention proceeds to "END" block 32, which terminates the method with the respect to the patient. This loop continues until the patient is fully evaluated.

The following Examples present the preferred embodiment of the present invention as a guide for use by a patient in assessing himself or herself for a psychiatric or emotional disorder and as an evaluation form for use by a mental health professional in conjunction with the guide for the patient. The guide is referred to herein as the "Patient Self-Assessment Guide". Personal pronouns, such as "you" and "your" or "I", "me" and "my", are meant to refer to a patient using the Guide or to a mental health professional using the Evaluation Form. While it is currently preferred that the Guide and Evaluation Form be used in hard copy or print medium, it also contemplated that the Guide and Evaluation Form can be presented in any suitable medium, including electronic media, such as via a computer terminal in the health care professional's office or via a secure WebSite using a suitable computer program. A suitable computer program automates the steps of the present invention. Thus, for example, a suitable computer program records all answers provided by the patient, directs patients to appropriate case studies based on their answers to initial questions, calculates totals of the values of the answers chosen by patients to questions, and establishes and displays a preliminary disorder indication to the patient after the patient has answered all the questions.

Certain aspects of the following Guide and Evaluation Form are described in terms of techniques and formats found or contemplated by the present inventor to work well in the practice of the invention. In light of the present disclosure and the general level of skill in the art, those of skill will appreciate that the following Guide is intended to be exemplary only and that numerous changes, modifications and alterations can be employed without departing from the spirit and scope of the invention.

EXAMPLE 1

Patient Self-Assessment Guide

Introduction

The Patient Self-Assessment Guide is designed to alert you to the possibility that you may have a psychiatric or emotional disorder.

There are many causes for each emotional disorder. Some are mainly psychological, others are mainly biological, and most result from a combination of both. For example, anxiety can result from a guilty conscience; and also it can result from a general medical condition (e.g., hyperthyroidism), caffeine, or low blood sugar. Another example is depression, which can result from a harsh conscience or from cancer of the pancreas.

Treatments for emotional disorders vary with the individual and with the causes of the disorder. For some people, the "talking cure"—analytically oriented psychotherapy or psychoanalysis—alone is adequate; indeed, most of us would benefit from this treatment sometime in our lives. For others, a combination of medical treatment and psychotherapy has proved helpful.

Many of the emotional disorders described in this guide are of the type that have been shown to respond to a combination of psychotherapy and medical treatment, including medication. This in no way implies that prescribed medication is a substitute for therapy. It can be a useful adjunct to it.

In order to rule out or identify any medical conditions that may be causing or adding to your present difficulties, you are strongly urged to have a thorough medical evaluation by your primary physician after completing this guide and before entering psychotherapy or psychoanalysis.

Warning

Under no circumstances should the Patient Self-Assessment Guide be considered a diagnostic tool. It is intended only to indicate whether or not you may have an emotional disorder and to facilitate a formal diagnosis of a psychiatric disorder by your health care professional.

In addition, while the Patient Self-Assessment Guide covers most major diagnostic categories, it does not cover them all. You may have a disorder that will not be suggested by this self-assessment.

Instructions

Turn to the next page, and fill out the "Personal Data Sheet."

Then answer the "Initial Questions" on pages 1 and 2. Answer all of these questions. For each "Yes" answer, continue to another page as instructed.

When completed, take this Guide to your healthcare provider. He or she can help you understand your difficulties. To facilitate this process, a *Further Evaluation and Summary Form for the Patient Self-Assessment Guide* is available for healthcare providers.

Personal Data Sheet

Today's Date \_\_\_\_\_\_\_\_\_\_\_\_\_\_\_\_\_\_\_\_\_\_\_\_\_
Name \_\_\_\_\_\_\_\_\_\_\_\_\_\_\_\_\_\_\_\_\_\_\_\_\_\_\_\_\_\_\_\_\_
Date of Birth \_\_\_\_\_\_\_\_\_\_\_\_\_\_\_\_\_\_\_\_\_\_\_\_
Address \_\_\_\_\_\_\_\_\_\_\_\_\_\_\_\_\_\_\_\_\_\_\_\_\_\_\_\_\_\_\_\_\_\_\_\_\_\_\_\_\_

Street

\_\_\_\_\_\_\_\_\_\_\_\_\_\_\_\_\_\_\_\_\_\_\_\_\_\_\_\_\_\_\_\_\_\_\_\_\_\_\_\_\_

City              State            Zip
Telephone Number:
  Day \_\_\_\_\_\_\_\_\_\_\_\_\_\_\_\_\_\_\_\_\_\_\_\_\_\_\_\_\_\_\_
  Evening \_\_\_\_\_\_\_\_\_\_\_\_\_\_\_\_\_\_\_\_\_\_\_\_\_\_\_

Please describe what is troubling you at this time and when it began (use the back of this sheet if necessary):
_________________________________________________
_________________________________________________
_________________________________________________
_________________________________________________
_________________________________________________

Have you had any physical illnesses and or injuries?

If so, please describe, and state when occurred:
_________________________________________________
_________________________________________________
_________________________________________________

What is the date of your last physical examination?
_________________________________________________

Are you currently taking any medications, vitamins, herbs and other substances? ___________________________.
If so, please list and date begun:
_________________________________________________
_________________________________________________

Have you had any psychological or emotional difficulties which required hospitalization? _______________
If so, please state your diagnoses:
_________________________________________________

Please describe any psychological or emotional difficulties any of your close relative have had, including parents, grandparents, brothers, sisters, aunts, uncles, and/or first cousins:
_________________________________________________
_________________________________________________

Marital Status (check):
( ) Single ( ) Married ( ) Divorced
Name children, if any, and their ages Employer:
What type of work do you do?
Have you had a major life change or environmental problem? For example:
___________Yes ___________No Has there been a death in your family?
___________Yes ___________No Has there been a divorce in your family?
___________Yes ___________No Are you a minority person and have you been treated unfairly?
___________Yes ___________No Do you feel that your educational level limits you?
___________Yes ___________No Have you lost a job or is your job stressful?
___________Yes ___________No Do you have adequate housing and food?
___________Yes ___________No Do you have access to good healthcare?
___________Yes ___________No Have you had any problems with the legal system?
If you answered "Yes" to any of the above questions, describe here:

Please estimate your overall functioning:
Range from 1–100:
100=Your functioning is superior despite your symptoms and problems.
75=You have slight impairment due to minor symptoms.
50=You have serious symptoms that impair your functioning (e.g., suicidal ideation, lengthy obsessional rituals).
25=You can barely function at your work or at home (impairment of functioning).
10=You cannot take care of your essential needs
Enter a score within range here _______________.

Enter a preliminary disorder indication or indications after completing the Guide.
_________________________________________________

Initial Questions

Please answer "Yes" or "No" to ALL questions on in this series of questions. Then, for all questions answered "Yes," proceed to actual case histories, as indicated by your answer, and read them.

1. Have you felt "blue" or "down" most of the time?
  No_______________. Yes_______________; Go to Case Study Nos. 1, 2 and 3 and read about Gale, Kirk and Laura.

2. Have you ever had (or are you having) an episode of depression when you lost interest in activities you once found enjoyable, and did it interfere with your ability to function?
  No_______________. Yes_______________; Go to Case Study Nos. 1, 2 and 3 and read about Gale, Kirk and Laura.

3. Has there been a period during which you felt "too" happy or "too" angry or irritable?
  No_______________. Yes_______________; Go to Case Study Nos. 1, 2 and 3 and read about Gale, Kirk and Laura.

4. Does your mood often fluctuate from happy to depressed?
  No_______________. Yes_______________; Go to Case Study Nos. 1, 2 and 3 and read about Gale, Kirk and Laura.

5. Do you drink alcohol?
  No_______________. Yes_______________; Go to Case Study No. 4 and read about Charles.

6. Have you ever taken "street" drugs or more of a medication than was prescribed?
  No_______________. Yes_______________; Go to Case Study No. 5 and read about Bob.

7. For women only: Do you have trouble with your menstrual periods?
  No_______________. Yes_______________; Go to Case Study No. 6 and read about Elle.

8. Are you troubled by thoughts you cannot get off your mind or by repetitive behaviors that you cannot control?
  No_______________. Yes_______________; Go to Case Study No. 7 and read about Sara.

9. Have you become intensely afraid for no obvious reason?
  No_______________. Yes_______________; Go to Case Study No. 8 and read about Fred.

10. Are you afraid of certain situations (for example, flying in an airplane, being in crowds, getting shots, being in a storm, getting bitten by a dog, having a fear of heights)?
  No_______________. Yes_______________; Go to Case Study No. 8 and read about Fred.

11. Are you afraid of being in public or doing activities in public, such as eating in front of people or speaking to strangers?
  No_______________. Yes_______________; Go to Case Study No. 8 and read about Fred.

12. Do you feel nervous, anxious, or "keyed up" a lot of the time?

No________. Yes________; Go Case Study No. 9 and read about Ernie.

13. Have you lost weight; or do you make yourself throw up or take laxatives after eating?

No________. Yes________; Go to Case Study No. 10 and read about Ann.

14. Has something awful or tragic ever happened to you (for example, being in a car accident, seeing your house burn down, being attacked or raped, seeing someone severely injured)?

No________. Yes________; Go to Case Study No. 11 and read about Al.

15. Have you had episodes when you forgot who you were, where you were, or what year it was?

No________. Yes________; Go to Case Study No. 12 and read about Jane.

Please continue with the next set of initial questions.

Initial Questions, continued

Unlike the questions on the preceding page, the questions below are not followed by instructions to go to another page for a diagnostic tree. Simply answer "yes" or "no" for all the questions below. Bring all "yes" answers to the attention of your healthcare provider for further evaluation.

16. Do you make careless mistakes (for instance, at school or work), or have difficulty completing tasks, or frequently lose objects? Are you usually unable to sit still, and do your thoughts ramble from one topic to another?

No________ Yes________

17. Do you believe that people are whispering about you, singling you out, intending to harm you, or controlling your thoughts?

No________ Yes________

18. Have you heard voices that others cannot hear?

No________ Yes________

19. Do you have any beliefs that others challenge (for instance, that you are being followed, or that a famous person is in love with you, or that your spouse is unfaithful?

No________ Yes________

20. Do you have any problems with your sexual life (for instance, impaired desire or arousal)?

No________ Yes________

21. Do you have any difficulties with your sleep that are not due to anxiety or depression (e.g., falling asleep unexpectedly, sleepwalking, waking up short of breath)?

No________ Yes________

22. Have you had physical problems that began before age 30 and which involve all of the following: your stomach and intestines; nervous system (for instance, seizures, paralysis, numbness, weakness, dizziness); sexual organs; and pain in at least 4 different parts of your body?

No________ Yes________

23. Have you ever had a problem with speeding, auto accidents, assaulting anyone, destroying property, taking items that were not yours, setting fires, repeatedly gambling, or investing more money than was wise?

No________ Yes________

24. Are you having trouble with your memory?

No________ Yes________

25. Do you have any major problems that started when you were an infant, child, or teenager (for example, learning disorders, physical impairments, difficulty speaking and/or writing)?

No________ Yes________

THANK YOU for taking the time to complete this Guide.

Case Study Nos. 1 and 2

Gale and Kirk

Depression

Case Study No. 1

Gale, a man in his mid-40s, said he had felt mildly to moderately depressed since he was a teenager. His thoughts were slowed down and he felt sad, guilty, worthless, and desperate. Seldom did he feel really well. Although his symptoms were troubling, they were never severe enough to result in hospitalization.

Gale had a type of moderately severe, chronic depression known as Dysthymia. He was successfully treated with psychotherapy and medication. He did not require hospitalization.

Check (√) one of the 3 sentences below that describes you best:

A. ________ Gale's history reminds me of myself a lot.

B. ________ Gale's history reminds me of myself a little.

C. ________ Gale's history does NOT remind me of myself at all.

If you checked A or B, describe below and continue.

NOTE: There is another type of depression known as Major Depression. It differs from Dysthymia in that it comes on suddenly and is more severe. Some people have both types.

Case Study No. 2

Kirk is an accomplished professional, who is known for his cheerfulness and optimism. At times his enthusiasm seemed excessive. He would become "too" high, elated, or irritable. In other words, he had episodes of hypomania. He never developed full-blown manic because the episodes lasted a few hours or days and never interfered with his ability to function.

Seemingly "out of the blue" Kirk started feeling depressed. Soon the simplest tasks seemed to overwhelm him. He drove his car slowly and seemed barely able to concentrate on driving. He spoke about imaginary failures and his dim future. Within a few days, he was unable to sleep, was pacing around the house and crying. He said that he felt trapped and that the only way out was suicide.

Kirk's diagnosis is Bipolar II Disorder because he a Major Depressive Episode and a history of hypomanic episodes. Kirk was successfully treated with hospitalization, medication and brief psychotherapy.

Check (√) one of the 3 sentences below that describes you best:

A. ________ Kirk's history reminds me of myself a lot. DESCRIBE BELOW AND CONTINUE NEXT PAGE.

B. ________ Kirk's history reminds me of myself a little. DESCRIBE BELOW AND CONTINUE NEXT PAGE.

C. \_\_\_\_\_\_\_\_\_\_\_ Kirk's history does NOT remind me of myself at all. CONTINUE NEXT PAGE.

Case Study No. 3

Laura

Hypomania and Manic

Laura's parents knew that something was wrong because Laura had not been sleeping. She had been singing theatrically, talking too fast, and had engaged herself in so many ongoing projects that she was unable to complete any of them. When her parents expressed concern and attempted to get her to slow down, she became furious. Late one night, Laura was driving while distracted and wrecked her car. The emergency room doctor admitted her to the psychiatry ward with a diagnosis of Mania.

Laura's parents described her as always appealing, full of energy, popular, talented, entertaining, and outgoing. On several occasions, though, she had been involved in too many projects, had stayed up too late, and was too energetic.

Laura's diagnosis was Bipolar I Disorder. Laura's treatment was very successful. For a while she took lithium, which slowed her behavior and thoughts. She also underwent psychoanalytically oriented psychotherapy, which helped her understand the insecurities that caused her excessiveness.

Check (√) one of the 3 sentences below that describes you best:

A. \_\_\_\_\_\_\_\_\_\_\_ Laura's history reminds me of myself a lot. DESCRIBE BELOW AND CONTINUE ON NEXT PAGE.

B. \_\_\_\_\_\_\_\_\_\_\_ Laura's history reminds me of myself a little. DESCRIBE BELOW AND CONTINUE ON NEXT PAGE.

C. \_\_\_\_\_\_\_\_\_\_\_ Laura's history does NOT remind me of myself at all. CONTINUE ON NEXT PAGE.

Gale, Kirk, Laura, and You (Continued)

If you, like Dale or Kirk, have been depressed, rate the frequency of your symptoms while depressed: 0=not at all or rarely; 1=occasionally; 2=frequently; 3=almost every day.

\_\_\_\_\_\_\_\_ 1. I felt sad, "down in the dumps," or blue. ("I'll never be better.")

\_\_\_\_\_\_\_\_ 2. I felt tired.

\_\_\_\_\_\_\_\_ 3. I felt worthless, inferior to others, and guilty ("I'm no good.").

\_\_\_\_\_\_\_\_ 4. I had trouble concentrating, remembering, and/or making decisions.

\_\_\_\_\_\_\_\_ 5. I often thought of killing myself.

\_\_\_\_\_\_\_\_ 6. I slept too little, or I sleep too much.

\_\_\_\_\_\_\_\_ 7. I walked or talked slowly.

\_\_\_\_\_\_\_\_ 8. I was agitated, irritable and fidgety.

\_\_\_\_\_\_\_\_ 9. I lost my ability to enjoy anything.

\_\_\_\_\_\_\_\_ 10. If you have lost or gained 5% of your body weight, enter a score of 3.

\_\_\_\_\_\_\_\_ TOTAL

A. \_\_\_\_\_\_\_ Yes. \_\_\_\_\_\_\_ No. Does Kirk remind you of yourself more than Gale?

B. \_\_\_\_\_\_\_ Yes. \_\_\_\_\_\_\_ No. Did your symptoms interfere with your work or relationships?

C. \_\_\_\_\_\_\_ Yes. \_\_\_\_\_\_\_ No. Was the onset of your depression preceded by abuse of alcohol or drugs?

Preliminary Disorder Indication:

If your answer is No for A, Yes for B, No for C, and your total score is 4–15, you may have Dysthymia.

If your answer is Yes for A, Yes for B, No for C, and your total score is 15 or more, you may have had a Major Depressive Episode (MDE).

If Laura reminded you of yourself, rate the frequency of your symptoms when you were high: 0=not at all or rarely; 1=occasionally; 2=frequently; 3=almost every day.

\_\_\_\_\_\_\_\_ 1. I got involved in so many projects that I had difficulty completing any of them.

\_\_\_\_\_\_\_\_ 2. I slept 4 hours or less a night.

\_\_\_\_\_\_\_\_ 3. I had sexual escapades that embarrass me or I spent money recklessly.

\_\_\_\_\_\_\_\_ 4. My mind was racing from one thought to another.

\_\_\_\_\_\_\_\_ 5. I talked a lot and wouldn't let anyone interrupt me.

\_\_\_\_\_\_\_\_ 6. If anyone challenged my ideas or my plans, I got agitated or irritable.

\_\_\_\_\_\_\_\_ 7. I thought more highly of my talents and abilities than now appears justified.

\_\_\_\_\_\_\_\_ TOTAL

A. \_\_\_\_\_\_\_ Yes. \_\_\_\_\_\_\_ No. Did your period of being too high or irritable last for a week or more?

B. \_\_\_\_\_\_\_ Yes. \_\_\_\_\_\_\_ No. Did your symptoms interfere with your work or relationships?

C. \_\_\_\_\_\_\_ Yes. \_\_\_\_\_\_\_ No. Was the onset of being too high or irritable preceded by abuse of alcohol or drugs?

Preliminary Disorder Indication:

If your total score is 8 or less; and if your answer is No for A, Yes for B, and No for C, you may have had an episode of Hypomania.

If your total score is 9 or more; and if your answer is Yes for A, Yes for B, and No for C, you may have had a Manic episode.

If you had an episode of Major Depression and Mania, you may have had a Mixed Episode.

Note: Episodes of Mania, Hypomanic, and Depression are the building blocks used to make the following diagnoses. To determine what type of mood disorder you may have, review the episodes you may have had and continue below.

Preliminary Disorder Indications:

Note: To meet the criteria for a disorder indication, you must check (√) all items below each diagnosis.

Major Depressive Disorder, Single Episode ( ) One Major Depressive Episode ( ) No manic episode, no a mixed episode, and no hypomanic episode.

Major Depressive Disorder, Recurrent ( ) Two or more Major Depressive Episodes.

( ) No manic episode, mixed episode or hypomanic episode.

Major Depressive Disorder with Seasonal Pattern ( ) Major Depressive Disorder.

( ) Depression begins in the fall or winter, lift when spring arrives.

( ) Depression during at least 2 of the past 5 fall/winter seasons.

Bipolar II Disorder ( ) One or more Major Depressive Episodes ( ) At least one episode of hypomania, but no episode of Mania.

Bereavement:

( ) Depression started soon after the death of a loved one.

Bipolar I Disorder, Single Manic Episode ( ) Only one manic episode ( ) No major depressive episodes.

Bipolar I Disorder, Most Recent Episode Hypomanic
( ) At least one Manic Episode
( ) Currently (or most recently) in a Hypomanic Episode.
Bipolar I Disorder, Most Recent Episode Manic
( ) Current or most recent episode is manic
( ) At least one major depressive episode, manic episode or mixed episode.
Bipolar I Disorder, Most Recent Episode Mixed
( ) Currently (or most recently) in a mixed episode
( ) At least one major depressive episode, manic episode or mixed episode.
Bipolar I Disorder, Most Recent Episode Depressed
( ) Currently (or most recently) in a Major Degressive Episode
( ) At least one Manic Episode or Mixed Episode.
Cyclothymic Disorder
( ) During the past 2 years, you had several some symptoms of hypomania and depressed that are not severely enough to meet the criteria for hypomania or major depressive episode
( ) You have never had a major depressive episode, manic episode or mixed episode.

Note: Return to the Personal Data Sheet and enter the disorder indication suggested above. This ends the comparison among you, Gale, Kirk and Laura.

Case Study No. 4

Charles (Alcohol Use/Abuse Disorder)

As a youngster, Charles swore that he would never drink because of the damage alcohol had done to his family. His mother abused alcohol and his father was Alcohol Dependent, i.e., "a full-blown alcoholic with binges and loss of jobs." But, as a teenager, Charles succumbed to peer pressure and broke his resolution never to drink. Vividly he remembers the first time he drank. He "felt high as a kite." His friends were surprised by how much he could drink. By the time Charles was in his early 20s, he kept a bottle with him wherever he went. "I knew I was in trouble when I drank half a fifth just to get ready for a party," he said. Charles entered psychotherapy, and found it helpful in understanding himself. But he needed more than psychotherapy. He joined Alcoholics Anonymous and is recovering.

Check (√) one of the 3 sentences below that describes you best:

A. \_\_\_\_\_\_\_\_ Charles's history reminds me of myself a lot.

B. \_\_\_\_\_\_\_\_ Charles's history reminds me of myself a little.

C. \_\_\_\_\_\_\_\_ Charles's history does NOT remind me of myself at all. STOP.

If you checked A or B, describe on back of this page and continue below.

Rate the frequency of your symptoms: 0=not at all or rarely; 1=occasionally; 2=frequently; 3=almost all the time.

\_\_\_\_\_\_\_\_ 1. I drink heavily when I'm upset.
\_\_\_\_\_\_\_\_ 2. I'm able to drink more than I used to.
\_\_\_\_\_\_\_\_ 3. I wake up the "morning after" and cannot remember what happened the night before.
\_\_\_\_\_\_\_\_ 4. I get anxious if I'm going to be at a place where there is no alcohol.
\_\_\_\_\_\_\_\_ 5. I feel guilty about my drinking.
\_\_\_\_\_\_\_\_ 6. I have a few drinks before the party begins.
\_\_\_\_\_\_\_\_ Add up your scores for 1–6.

Preliminary Disorder Indication:
Alcohol Abuse Disorder if your total score is 1–5.
Alcohol Dependence, early stage, if your total score is 6 or more.

Rate the frequency of your symptoms: 0=not at all or rarely; 1=occasionally; 2=frequently; 3=almost all the time.

\_\_\_\_\_\_\_\_ 1. I continue to drink despite stern warnings from family or friends.
\_\_\_\_\_\_\_\_ 2. I decide to have one drink, but end up intoxicated.
\_\_\_\_\_\_\_\_ 3. I often wish I could stop drinking.
\_\_\_\_\_\_\_\_ 4. I have switched from one brand to another to control my drinking.
\_\_\_\_\_\_\_\_ 5. I waste time because of drinking.
\_\_\_\_\_\_\_\_ 6. I avoid family or friends because I drink.
\_\_\_\_\_\_\_\_ 7. I wake up during the night after drinking too much.
\_\_\_\_\_\_\_\_ 8. I don't eat well when I'm drinking.
\_\_\_\_\_\_\_\_ 9. I have "blackouts," or periods of forgetfulness, after drinking.
\_\_\_\_\_\_\_\_ 10. I drink an "eye opener" the morning after.
\_\_\_\_\_\_\_\_ TOTAL Preliminary Disorder Indication:
Alcohol Dependence, middle phase if your total score of 1–13.
Alcohol Dependence, late phase if your total score is 14 or more.

Case Study No. 5

Bob

Non-Alcohol Use/Abuse Disorder

Bob was described as "a worrier." As a youngster, he was overly conscientious. He worried that his handwriting was sloppy and that his clothes were dirty. He was afraid he would make his parents unhappy. "I was a good kid, but when I started experimenting with pot, I felt a great sense of relief and I understood where the term 'mellow' came from. I didn't worry so much anymore." Soon he was smoking marijuana several times a week. He lost his initiative to achieve, and he spent so much time looking for drugs that his school work suffered. He felt guilty and wanted to stop, but could not. Unfortunately, Bob became addicted to several drugs, and, finally, was hospitalized.

Check (√) one of the 3 sentences below that describes you best:

\_\_\_\_\_\_\_\_ A. Bob's history reminds me of myself a lot.
\_\_\_\_\_\_\_\_ B. Bob's history reminds me of myself a little.
\_\_\_\_\_\_\_\_ C. Bob's history does NOT remind me of myself at all. STOP.

If you checked A or B, describe on back of this page and continue below.

Rate the frequency of your symptoms: 0=not at all or rarely; 1=occasionally; 2=frequently; 3=almost all the time.

\_\_\_\_\_\_\_\_ 1. I find that I use more drugs than I intend to.
\_\_\_\_\_\_\_\_ 2. I use drugs for a longer period of time than I intend to.
\_\_\_\_\_\_\_\_ 3. I try to stop taking drugs without success.
\_\_\_\_\_\_\_\_ 4. I continue to take a drug(s) despite recognizing that it is harmful.
\_\_\_\_\_\_\_\_ 5. I take more of the drug to get the desired effect.
\_\_\_\_\_\_\_\_ 6. I take the drug to avoid symptoms of withdrawal.

_______ 7. I don't eat well when I do use drugs.
_______ 8. I avoid family or friends because I use drugs.
_______ 9. People treat me unfairly.
_______ TOTAL
Preliminary Disorder Indication:
Drug Abuse Disorder if your total score is 1–8.
Drug Dependence if your total score is 9 or more.

Case Study No. 6

Elle

Severe Premenstrual Syndrome

Elle, 38, said that almost all of her menstrual periods had been "terrible" since she was 16. She would become intolerably irritable and sad, and she had severe cramps during the week before her period. For a day or two a month, she could not attend school. Later she avoided volunteering in her daughter's class for fear that she would lose her temper and slap one of the children. After her periods started, Elle felt fine and got along well with her husband and daughter.

Elle tried to get help for her troublesome periods. She told her mother, who, although usually sympathetic, dismissed her complaints by saying: "I never had any problem like that. It must all be in your mind." Elle consulted a gynecologist, who ordered tests and treated her with birth control pills, diet, and exercise, with no relief. He referred her to a mental health professional, who told her that her PMS was due to her not wanting to be a woman.

Elle's diagnosis is Premenstrual Dysphoric Disorder which is a type of severe PMS in which mood disturbance is prominent. After receiving medical treatment, Elle is free of PMS symptoms. Her husband and daughter are astounded by her improvement.

Check (√) one of the 3 sentences below that describes you best:
A. _______________ Elle's history reminds me of myself a lot. DESCRIBE BELOW.
B. _______________ Elle's history reminds me of myself a little. DESCRIBE BELOW.
C. _______________ Elle's history does NOT remind me of myself at all. STOP.

Rate the frequency of your symptoms during the week before your period: 0=never or rarely; 1=occasionally; 2=frequently; 3=almost every day.
_______ 1. I feel a sense of doom, depression, and low self-esteem.
_______ 2. I become "keyed up," or tense.
_______ 3. My feelings change suddenly (e.g., from sadness to irritability).
_______ 4. I become easily angered and "blow up" at people.
_______ 5. I lose interest in work, school, friends, or hobbies.
_______ 6. I have difficulty keeping my mind on a task.
_______ 7. I tire easily, lack energy or feel exhausted.
_______ 8. I overeat and crave specific foods.
_______ 9. I sleep too much or too little.
_______ 10. I feel overwhelmed or out of control.
_______ 11. I have physical symptoms, such as breast tenderness or swelling, headaches, joint or muscle pain, a sensation of "bloating," cramping, or weight gain.
_______ TOTAL
Preliminary Disorder Indication:
Premenstrual Dysphoric Disorder, possible if your total score is 13–19.
Premenstrual Dysphoric Disorder, probable if your total score is 20 or more.

Case Study No. 7

Sara

Obsessive Compulsive Disorder

Sara's life was controlled by rituals. Her showers took as long as 3 hours. She was compelled to wash each arm 8 times in a certain rhythmical fashion. If she forgot whether she had washed her arm an even or an odd number of times, she began the ritual again. She could not stop washing on an odd number because she feared a family member might become ill. She knew her rituals weren't rational, but she was unable to dispel them from her mind. Sara was bothered by many other obsessions and compulsions. For example, she would get certain songs "on (her) mind until it almost drove (her) out of (her) mind."

Sara's diagnosis was obsessive compulsive disorder. She was successfully treated with medication and psychotherapy.

Check (√) one of the 3 sentences below that describes you best:
A. _______________ Sara's history reminds me of myself a lot. DESCRIBE BELOW.
B. _______________ Sara's history reminds me of myself a little. DESCRIBE BELOW.
C. _______________ Sara's history does NOT remind me of myself at all. STOP.

Rate the frequency of your symptoms: 0=not at all or rarely; 1=occasionally; 2=frequently; 3=almost all the time.
_______ 1. I wonder if I have left the oven on, or if I have left the alarm set when I leave home.
_______ 2. I count things for no reason.
_______ 3. I think over and over of doing something violent and obscene.
_______ 4. I get certain words, phrases, or images in my mind and can't get them out.
_______ 5. I say the same sentence more than once.
_______ 6. I count and cannot stop counting during certain activities (e.g., when taking a shower).
_______ TOTAL
Preliminary Disorder Indication:
Obsessive Disorder, possible, if your total score is 3–7.
Obsessive Disorder, probable, if your total score is 8 or more.

Case Study No. 7

Sara, continued

Obsessive Compulsive Disorder

Are you troubled by repetitive behaviors, such as washing your hands, checking locks, or counting?
_______________ No. STOP.
_______________ Yes. If Yes, describe:
If "Yes," rate the frequency of these behaviors in the questions below: 0=not at all or rarely; 1=occasionally; 2=frequently; 3=almost all the time.
_______ 1. I wash my hands after I have been around, but have not touched, something dirty.
_______ 2. I touch whatnots to make sure they are in their right place.
_______ 3. My repetitive behaviors or "habits" bother other people.

______ 4. I'm afraid of being contaminated in public places (e.g., by sitting on public seats).
______ 5. I clean utensils with napkins before eating.
______ 6. I touch my toothbrush or other items several times before or after I use them.
______ 7. I double-check to make sure mail has fallen into the mailbox.
______ 8. I spend a lot of time cleaning and thinking about cleaning.
______ 9. I get upset if anyone messes up what I have arranged.
______ TOTAL
Preliminary Disorder Indication:
Compulsive Disorder, possible if your total score is 5–13.
Compulsive Disorder, probable if your total score is 14 or more.

Case Study No. 8

Fred

Panic Disorder and Phobias

Fred was having dinner with his boss when, out of the blue, he was struck with an awful terror. He felt electric-like currents surge down his arms, his heart started pounding, and he was short of breath. He thought he was going to faint, lose control of his bowels and wet himself. He was sure he was having a heart attack. He was rushed to the emergency room, where a diagnosis of Panic Attack was made.

Fred was afraid he would have another panic attack and embarrass himself by vomiting or losing control of his bowels. To control the anticipated anxiety attack, he always sat in an aisle seat. But, he became afraid that he would have an attack during takeoff or landing, while the seatbelt sign was on, and would be unable to get to a restroom. The thought terrified him and he stopped traveling. He rejected a promotion that would have required him to travel.

As a child he was terrified of needles (Specific Phobia). Although an excellent student, he was terrified to speak in front of the class. Invariably, when called upon to do so, he had panic-like attacks.

Check (√) one of the 3 sentences below that describes you best:

A. ______________ Fred's history reminds me of myself a lot. DESCRIBE BELOW.

B. ______________ Fred's history reminds me of myself a little. DESCRIBE BELOW.

C. ______________ Fred's history does NOT remind me of myself at all. STOP.

If you checked A or B, describe on back of this page and continue below.

Rate the severity of your symptoms when you are having a panic attack: 0=not at all or mild; 1=moderate; 2=severe.
______ 1. My heart races and pounds.
______ 2. I break out in a sweat.
______ 3. I tremble. My hands shake.
______ 4. I'm afraid I cannot get my breath.
______ 5. I feel as if I'm choking.
______ 6. I have chest pain.
______ 7. I feel as if I'm going to throw up.
______ 8. I feel light-headed as if I'm going to faint.
______ 9. I feel unreal or separated from myself.
______ 10. I'm afraid I'm losing my mind.
______ 11. I'm afraid I'm dying.
______ 12. My hands and feet tingle.
______ 13. I have chills or hot flashes.
______ TOTAL
Preliminary Disorder Indication:
______________ A score of 0–9 suggests that you probably have not had a Panic Attack.
______________ A score of 10 or more suggests that you probably have had a Panic Attack.
If your score is 0–9, answer the questions below:
A. Do you become anxious in certain situations (for example, flying in an airplane, being in crowds, getting a shot or seeing blood, being in a storm, getting bitten by a dog, having a fear of heights)?
______ Yes ______ No
Preliminary Disorder Indication:
If you answered "yes", you probably have a Specific Phobia.
B. Are you afraid of situations that involve people (for example, eating in public, fearful of asking strangers directions, getting extremely nervous before making an announcement to a group), and does this fear interfere with your work or relationships?
______ Yes ______ No
Preliminary Disorder Indication:
If you answered "yes", you probably have a Social Phobia.
If your score is 10 or more, answer the questions below:
C. Have you had more than one Panic Attack?
______ Yes ______ No
D. Have you have worried for one month of more that you will have another attack, or that the attack means something awful will happen (e.g., lose you mind, die), or you have changed your behavior (for example, refused to go to work or school)?
______ Yes ______ No
E. Was your attack of anxiety preceded by ingestion of a substance, e.g. caffeine, MSG, or any medication?
______ Yes ______ No
Preliminary Disorder Indication:
If you answered "yes" to questions C, D and E, you probably do not have a Panic Disorder.
If you answered "yes" to questions C and D, BUT "no" to question E, you probably have a Panic Disorder.
If the results immediately above suggested you probably have a Panic Disorder, answer the following questions:
F. Are you afraid of being trapped in a certain situation from which you cannot easily escape and in which you might be embarrassed.
______ Yes ______ No
G. If yes, do you avoid the situations you fear, thinking it might bring on a panic attack or make you very anxious?
______ Yes ______ No
Preliminary Disorder Indication:
If you answered "yes" to questions F and G, you probably have Panic Disorder With Agoraphobia
If you answered "yes" to questions F, BUT "no" to question G, you probably have Panic Disorder Without Agoraphobia
Did you answer "yes" to question G above?
______ Yes ______ NO
Preliminary Disorder Indication:
If you answered "yes," you may have Agoraphobia.
Did you answer "yes" to question G above, BUT "no" to question C above?
Preliminary Disorder Indication:
If you answered "yes", you may have Agoraphobia Without History of Panic Disorder.

Case Study No. 9

Ernie

Generalized Anxiety Disorder

It was obvious to Ernie, and to everyone around him, that he was uptight. He always walked fast, he fidgeted with his pencil, and he picked at his hair. He exhausted himself by worrying, and he developed physical symptoms: he trembled, his chest felt tight, and his heart raced. He consulted his doctor who gave him a clean bill of physical health but made the diagnosis of Generalized Anxiety Disorder.

If some part of Ernie's story reminds you of yourself, and if you have worried excessively for more days than not during the last 6 months, continue.

Have you found it difficult to control your nervousness? If "Yes," continue. If, "no," STOP.

Check (√) one of the 3 sentences below that describes you best:

A. \_\_\_\_\_\_\_\_\_\_\_\_\_\_ Ernie's history reminds me of myself a lot.

B. \_\_\_\_\_\_\_\_\_\_\_\_\_\_ Ernie's history reminds me of myself a little.

C. \_\_\_\_\_\_\_\_\_\_\_\_\_\_ Ernie's history does NOT remind me of myself at all. STOP.

If you checked A or B, describe and continue.

Rate the frequency of your symptoms: 0=not at all or rarely; 1=occasionally; 2=frequently; 3=almost all the time.
\_\_\_\_\_\_\_\_ 1. I feel restless and keyed up.
\_\_\_\_\_\_\_\_ 2. I become tired easily.
\_\_\_\_\_\_\_\_ 3. I forget what I was thinking.
\_\_\_\_\_\_\_\_ 4. I am irritable and snap at people.
\_\_\_\_\_\_\_\_ 5. My muscles are tight and/or sore.
\_\_\_\_\_\_\_\_ 6. I have difficulty falling asleep or wake up soon after falling asleep.
\_\_\_\_\_\_\_\_ TOTAL Preliminary Disorder Indication:

Generalized Anxiety Disorder, possible if your total score is 6–14.

Generalized Anxiety Disorder, probable if your total score is 15 or more.

Case Study No. 10

Ann

Eating Disorders (Anorexia and/or Bulimia)

Ann was distressed when her breasts began to develop. She became even more distressed when her periods started. She felt her mother had never loved her, and now that she was becoming a young woman, she would never get the love for which she longed. She wanted her mother's love, symbolized by food, and at the same time rejected it. She felt so big and ugly. All the fashion magazines glamorized thinness. Ann started to diet. Her mother threatened to beat her unless she ate and would not allow her to leave the table until she had eaten. When her mother was not looking, she would give food to her dog. After her plate was clean, she would go to the bathroom and make herself vomit. After 3 or 4 days of fasting, she was no longer hungry, and her mood was elevated. She lost weight and was taken to her family doctor, who hospitalized her.

Check (√) one of the 3 sentences below that describes you best:

A. \_\_\_\_\_\_\_\_\_\_\_\_\_\_ Ann's history reminds me of myself a lot.

B. \_\_\_\_\_\_\_\_\_\_\_\_\_\_ Ann's history reminds me of myself a little.

C. \_\_\_\_\_\_\_\_\_\_\_\_\_\_ Ann's history does NOT remind me of myself at all. STOP.

If you checked A or B, describe on the back of this page and continue.

Rate the frequency of your symptoms: 0=not at all or rarely; 1=occasionally; 2=frequently; 3=almost all the time.
\_\_\_\_\_\_\_\_ 1. I am afraid of getting fat.
\_\_\_\_\_\_\_\_ 2. I look at myself in the mirror to see if I'm gaining weight.
\_\_\_\_\_\_\_\_ 3. I think that my legs or buttock are too large.
\_\_\_\_\_\_\_\_ 4. I believe that losing weight is noble or a sign of strength.
\_\_\_\_\_\_\_\_ TOTAL Disorder indication:

Anorexia Nervosa if your total score is 9 or more. Continue.

Ann and You (Continued)

Binge Eating

Do you have episodes, lasting less than 2 hours, when you eat until you're uncomfortably full? Have you ever had 2 such episodes in the same week? If "Yes," to both questions, describe on the back of this page and continue below.

Rate the frequency of your symptoms when binge eating: 0=not at all or rarely; 1=occasionally; 2=frequently; 3=almost all the time.
\_\_\_\_\_\_\_\_ 1. I eat fast and am in a frenzy or trance-like state when binge eating.
\_\_\_\_\_\_\_\_ 2. I cannot control myself when I start binge eating.
\_\_\_\_\_\_\_\_ 3. I induce vomiting or take laxatives after binge eating.
\_\_\_\_\_\_\_\_ 4. I exercise excessively to burn off calories.
\_\_\_\_\_\_\_\_ 5. I prefer sweets like doughnuts, ice cream and pie.
\_\_\_\_\_\_\_\_ 6. I am likely to binge eat after being rejected.
\_\_\_\_\_\_\_\_ 7. I eat alone because I'm embarrassed by my eating habits.
\_\_\_\_\_\_\_\_ 8. I feel disgusted with myself for overeating.
\_\_\_\_\_\_\_\_ TOTAL Preliminary Disorder indication:

Binge-Eating Disorder, possible if your total score is 6–11.

Binge-Eating Disorder, probable if your total score is 12 or more.

Case Study No. 11

Al

Acute Stress Disorder and Post-Traumatic Stress Disorder

Some people have Acute Stress Disorder, which develops soon after an awful incident, and Post-Traumatic Stress Disorder which develops later. To help you determine if you have either of these disorders, the following vignette is presented:

Al was severely injured in an explosion in Vietnam. Several of his fellow soldiers were killed. When help arrived, Al was dazed and sitting still, as if paralyzed. When he was asked to describe the incident, a blank stare came over his face, and he described the incident as if he had not been there.

After he returned to the United States, he started having flashbacks of the battlefield killing. His pulse raced, he breathed heavily, and he was terrified. Numerous places and incidents reminded Al of the tragedy. For example, when he heard a car backfire, he would "see" the explosion again. Al started to avoid situations that would remind him of the war.

If Al's tragic situation reminds you of an incident you have experienced, and if it occurred within the past month, describe it on the back of this page, including date that the incident occurred.

Check (√) one of the 3 sentences below that describes you best:

A. _______________ Al's history reminds me of myself a lot. If you checked A, describe below and continue.

B. _______________ Al's history reminds me of myself a little. If you checked B, describe below and continue.

C. _______________ Al's history does NOT remind me of myself at all. STOP.

Rate the frequency of your symptoms: 0=not at all or rarely; 1=occasionally; 2=frequently; 3=almost all the time.

_______ 1. I felt numb, as if I was separated from the incident.
_______ 2. I felt dazed or in a fog.
_______ 3. I felt it was not real and/or it was occurring in slow motion.
_______ 4. I felt as if I were outside the experience and was observing it.
_______ 5. I cannot remember certain aspects of the incident.
_______ TOTAL A. Yes_______. No_______. Do you "relive" the incident in dreams, flashbacks, or do you become distressed when remembering the event?

B. Yes_______. No_______. Do you avoid people, places or things that might remind you of the incident?

C. Yes_______. No_______. Are you more anxious than you used to be as evidenced by poor sleep, sweating, trembling, and exaggerated startle response?

Preliminary Disorder Indication:

If your total score is 4 or more, if the incident occurred within the past month, and if you may answered Yes to A, B, and C, you probably have Acute Stress Disorder. Continue.

_______ 6. When I think about the event, as when I wrote about it above, I have flashbacks.
_______ 7. I have nightmares of the incident.
_______ 8. When I recall the incident, I breathe fast or tremble.
_______ 9. I avoid reminders of the incident.
_______ 10. I am unable to remember certain parts of the incident
_______ 11. I have withdrawn from life.
_______ 12. My feelings are flattened.
_______ 13. I feel detached from my surroundings.
_______ 14. I feel that I'm doomed.
_______ 15. I have difficulty falling asleep or staying asleep.
_______ 16. I have outbursts of anger.
_______ 17. I "jump out of my skin" when surprised.
_______ TOTAL Preliminary Disorder Indication:

Post-Traumatic Stress Disorder if your total score is 10 or more, if the incident occurred more than a month ago, and if you may answered Yes to A, B, and C.

Case Study No. 12

Jane

Multiple Personality Disorder

Since childhood, Jane had episodes when she would "come to" and wonder who she was, where she was, and what had happened. Her surroundings seemed unreal. She said it was similar to "highway hypnosis" (i.e., realizing that you have traveled many miles without remembering it). Her pervasive lack of connectedness was not due to drugs, alcohol, or a seizure disorder.

After a suicide attempt, Jane was hospitalized and treated with medication and long-term psychotherapy. She learned that she had been sexually and physically abused as a child. She had been too small to run away from home; therefore, "instead my mind ran away from situations that I couldn't face. I would travel to other places and earlier times and forget who I was." Her episodes of disconnection (e.g., forgetting, changing identity, detachment from the external world) were ways of defending herself against intolerable realizations.

Check (√) one of the 3 sentences below that describes you best:

A. _______________ Jane's history reminds me of myself a lot. If you checked A, describe on back and continue.

B. _______________ Jane's history reminds me of myself a little. If you checked B, describe on back and continue.

C. _______________ Jane's history does NOT remind me of myself at all. STOP.

Rate the frequency of your symptoms: 0=not at all or rarely; 1=occasionally; 2=frequently; 3=almost all the time.

_______ 1. I feel like a small child.
_______ 2. Others people have been surprised by the shifts in my personality (e.g., "You went into the bathroom as one person and came out another.")
_______ 3. Different personalities control my behavior at different times.
_______ 4. I forget who I am, and I can't remember certain events.
_______ 5. I find clothes I don't remember buying.
_______ 6. I find credit card charges I don't remember making.
_______ 7. I withdraw into myself and put a barrier between me and others to protect myself.
_______ 8. I have more than one personality.
_______ 9. I go into trances for no apparent reason.
_______ 10. I feel that I don't inhabit my own body.
_______ 11. I look at the mirror and am confused by whom I see.
_______ TOTAL Preliminary Disorder Indication:

Dissociative Identity Disorder, probable (formerly Multiple Personality Disorder),if your total score is 16 or more and you have assumed a different identity.

Note: If you answered "Yes" to several Initial Questions (on page 1 and 2), that is further evidence suggesting Dissociative Identity Disorder.

Dissociative Amnesia if you are unable inability to recall important personal information.

Depersonalization Disorder if you detach from yourself.

Dissociative Fugue if you detach from the external world and run away.

EXAMPLE 2

Mental Health Professional's Evaluation Form for
Use with the Patient Self-Assessment Guide for
Psychiatric Disorders Introduction The purpose of the Patient Self-Assessment Guide for Psychiatric Disorders is twofold:

(1) For the persons troubled by emotional difficulties, the Guide is intended to help them more clearly identify and understand their problems, and to encourage them to become involved in decisions affecting their health care.

(2) For healthcare providers, the Guide and this Evaluation Form is intended to provide documentation that the major psychiatric disorders which are part of a thorough psychiatric examination have been evaluated, thus allowing the health professional more time to concentrate on the person and his or her individual difficulties within the broader framework of the diagnostic category.

Definitions of Psychiatric Disorders

Psychiatric disorders are described from five perspectives or axes, and are defined in the fourth edition of the *Diagnostic and Statistical Manual of Mental Disorders* (*DSM-IV*™) and published by the American Psychiatric Association.

Axis I disorders are major psychiatric disorders, except for Personality Disorders and Mental Retardation. Many Axis I disorders respond to treatment with medication. Axis II comprises Personality Disorders and Mental Retardation. Axis III is for reporting general medical conditions that may affect psychiatric disorders. Axis IV is for reporting environmental and social problems. Axis V is an overall assessment of functioning.

The DSM-IV categories were used in the development of this Guide since they were formulated by over 1000 mental health professionals and members of numerous professional organizations on the basis of clinical research, field trials and extensive review of the literature. Most healthcare providers think that an evaluation of an emotionally troubled person is not thorough unless the DSM-IV categories have been carefully considered.

Disorders Emphasized in Guide

The Guide focuses on the Axis I or major psychiatric disorders that are amenable to detailed self-assessment. The assessment of these disorders begins with initial questions, which are followed by a diagnostic tree. The codes for the diagnoses suggested are given in Part 1 of this form.

There are other Axis I disorders which are not amenable to extensive self-assessment for various reasons. Certain diagnoses (e.g., psychosis) can be overwhelming to the person undertaking self-assessment. Other diagnoses (e.g., sexual and gender identity disorders) go far beyond the scope of any questionnaire. Still other diagnoses (e.g., dementia, delirium) are impossible to evaluate by self-assessment. The Guide attempts, however, to provide a starting point for an evaluation of these disorders, which are not followed by a diagnostic tree. Codes for these preliminary diagnoses are found in Part 2 of this form.

INSTRUCTIONS

1. Give your patient or client the Guide and ask him or her to complete it.

2. The person may feel objectified and dealt with coldly when asked to complete the Guide. To decrease this possibility, explain to the person that the Guide is intended to help the person and the healthcare provide establish a working relationship. The Guide will help the person see in what sort of general area his or her problems lie, and that both of you will use this knowledge to begin exploring the specific, individual aspects of his or her present difficulties.

3. When possible, have the person complete the Guide before the first visit, preferably in the privacy of his or her own home or wherever he or she feels most comfortable.

4. Tell the person to take as much time answering the questions as he or she wishes.

5. If the person is very upset, you may suggest that it is acceptable to have help filling out this guide from someone whom the person trusts.

6. Remind the person to bring the Guide to the next appointment.

7. Attach the Guide to the Evaluation Form to complete the document.

EVALUATION

Person's name_____________________________

Date Guide Completed__________________

Part 1

Self-Assessment Disorders

Instructions

1. Check to see if every "yes" answer to INITIAL QUESTIONS 1–15 was followed by a completed diagnostic page or section. If not, ask the person the remaining questions, and record the answers on the incomplete pages.

2. Transfer answers from the boxes in the Guide that are checked (√) to diagnoses listed below.

CHRONIC DEPRESSION

__________________ Dysthymia 300.4

[Chronic Depression]

MAJOR DEPRESSION

__________________ Major Depressive Disorder, Single Episode 296.2X

Ask the person if he or she has had only one depressive episode.

__________________ Bereavement

__________________ Major Depressive Disorder, Recurrent 296.3X

Ask the person if he or she has had only one depressive episode.

__________________ Major Depressive Disorder, Recurrent 296.3X, with Seasonal Pattern __________________ Bipolar II Disorder 296.89

Recurrent Major Depression With Hypomanic Episodes and NO manic episode.)

Note: If the person is schizophrenic or psychotic, these diagnoses do not apply.

MANIC/HYPOMANIC EPISODE

Explanation: A person has Bipolar I Disorder if he or she has had at least one manic episode that was not caused by misuse of drugs or alcohol. The coding of the subtype of Bipolar I Disorder depends on the nature of the most recent episode, which should be apparent during the interview. For example, if the person has a history of Mania and currently is depressed, the diagnosis is Bipolar I Disorder, Most Recent Episode Depressed.

__________________ Bipolar I Disorder, Single Manic Episode 296.0x

Only on manic episode and no major depressive episodes.

__________________ Bipolar I Disorder, Most Recent Episode Hypomanic 296.40

At least one Manic Episode and most recent episode is hypomanic.

__________________ Bipolar I Disorder, Most Recent Episode Manic 296.4X

Current or most recent episode is manic.

__________________ Bipolar I Disorder, Most Recent Episode Mixed 296.6x

A history of Mania, and the most recent episode is mixed. (A mixed episode is the presence of symptoms of depression and elation that do not meet the criteria for Major Depression or Mania.)

\_\_\_\_\_\_\_\_\_\_ Bipolar I Disorder, Most Recent Episode Depressed 296.6x

Most recent episode is Major Depressive Episode.
\_\_\_\_\_\_\_\_\_\_ Cyclothymic Disorder 301.13

ALCOHOL ABUSE/DEPENDENCE DISORDER
\_\_\_\_\_\_\_\_\_\_ Alcohol Abuse 305.00
\_\_\_\_\_\_\_\_\_\_ Alcohol Dependence 303.90

For specific coding for Alcohol-induced Disorders (e.g., Dementia, Anxiety), see DSM-IV, pages 195–284.

NON-ALCOHOL ABUSE/DEPENDENCE DISORDER
\_\_\_\_\_\_\_\_\_\_ Drug Abuse Disorder
\_\_\_\_\_\_\_\_\_\_ Drug Dependence For coding of specific substances (e.g., amphetamine, caffeine), see DSM-IV, pages 16–19.

SEVERE PREMENSTRUAL SYNDROME
\_\_\_\_\_\_\_\_\_\_ Premenstrual Dysphoric Disorder (No code. This has not been included as an official diagnosis in DSM-IV, but rather as a research disorder.)

OBSESSIVE COMPULSIVE DISORDER
\_\_\_\_\_\_\_\_\_\_ Obsessive Compulsive Disorder 300.3

PHOBIAS AND PANIC DISORDERS
\_\_\_\_\_\_\_\_\_\_ Specific Phobia 300.29
\_\_\_\_\_\_\_\_\_\_ Social Phobia 300.23
\_\_\_\_\_\_\_\_\_\_ Panic Disorder With Agoraphobia 300.21
\_\_\_\_\_\_\_\_\_\_ Panic Disorder Without Agoraphobia 300.01
\_\_\_\_\_\_\_\_\_\_ Agoraphobia Without a History of Panic Disorder 300.22

GENERALIZED ANXIETY DISORDER
\_\_\_\_\_\_\_\_\_\_ Generalized Anxiety Disorder 300.02

EATING DISORDERS (ANOREXIA AND/OR BULIMIA)
\_\_\_\_\_\_\_\_\_\_ Anorexia Nervosa 307.1
\_\_\_\_\_\_\_\_\_\_ Bulimia Nervosa 307.51

ACUTE STRESS DISORDER AND POST-TRAUMATIC STRESS DISORDER
\_\_\_\_\_\_\_\_\_\_ Acute Stress Disorder 308.3
\_\_\_\_\_\_\_\_\_\_ Post-Traumatic Stress Disorder 309.81
\_\_\_\_\_\_\_\_\_\_ Adjustment Disorder 309.xx NOTE: This diagnosis does not appear in the Guide as the patient is likely to confuse this stress that leads to Acute Stress Disorder with Adjustment Disorder. Adjustment Disorder is defined as emotional symptoms that develop within 3 months of a major stress, and the disturbance does not meet the criteria for a disorder and it is not caused by bereavement.

MULTIPLE PERSONALITY DISORDER
(Dissociative Disorders is the more recent term.)
\_\_\_\_\_\_\_\_\_\_ Dissociative Amnesia 300.12
\_\_\_\_\_\_\_\_\_\_ Dissociative Fugue 300.13
\_\_\_\_\_\_\_\_\_\_ Dissociative Identity Disorder 330.14 (Multiple Personality Disorder.)
\_\_\_\_\_\_\_\_\_\_ Depersonalization Disorder 300.6
\_\_\_\_\_\_\_\_\_\_ Dissociative Disorder NOS (limited symptom of one of above.)

Part 2

Disorders NOT Self-Assessed

Instructions:
1. Check to see if the person answered "yes" to any of the INITIAL QUESTIONS 16–25 on page 2 of the Guide.
2. Transfer all "yes" answers to the spaces next to the diagnoses below.
3. Use these answers to begin your process of finding a preliminary diagnosis.

QUESTION 16. (Careless mistakes, difficulty sitting still ...)
\_\_\_\_\_\_\_\_\_\_ Attention-Deficit/Hyperactivity Disorder 314.xx QUESTION 17. (People whispering ...)
\_\_\_\_\_\_\_\_\_\_ Schizophrenia Schizophreniform Disorder Schizoaffective Disorder 295.xx QUESTION 18. (Heard voices that others cannot hear ...)
\_\_\_\_\_\_\_\_\_\_ Schizophrenia Schizophreniform Disorder Schizoaffective Disorder 295.xx QUESTION 19. (Delusions that are similar to real situations e.g., being followed, jealousy ...)
\_\_\_\_\_\_\_\_\_\_ Delusional Disorder 297.1

QUESTION 20. (Problems with your sexual life ...)
\_\_\_\_\_\_\_\_\_\_ Sexual and Gender Identity Disorders 302.xx QUESTION 21. (Sleep problems ...)
\_\_\_\_\_\_\_\_\_\_ Sleep Disorders 307.xx QUESTION 22. (Physical problems before age 30 ...)
\_\_\_\_\_\_\_\_\_\_ Somatoform Disorders, Factitious Disorders, Hypochondriasis, Malingering 300.x QUESTION 23. (Car accidents, assaulting anyone ...)
\_\_\_\_\_\_\_\_\_\_ Impulse Control Disorder 312.xx QUESTION 24. (Trouble with memory ...)
\_\_\_\_\_\_\_\_\_\_ Delirium and Dementia 293

QUESTION 25. (Disorders that started when you an infant, child or teenager ...)
\_\_\_\_\_\_\_\_\_\_ Disorders Usually First Diagnosed in Infancy, Childhood, or Adolescence NOTE: Some of these disorders include Mental Retardation, Learning Disorders, Motor Skills Disorder, Communication Disorder, and Developmental Disorder.

SUMMARY

I have reviewed the Patient Guide for Self-Assessment of Psychiatric Disorders and completed the attached Evaluation Form. Based on my personal interview of \_\_\_\_\_\_\_\_\_\_minutes with this person, I have concluded the following:

Axis I: Major Disorder Diagnoses

The preliminary disorder indications suggested by the Guide are confirmed by my interview.
\_\_\_\_\_\_\_\_\_\_Yes \_\_\_\_\_\_\_\_\_\_No If "No," explain:

Axis II: Personality Disorder Diagnosis(es)
Check any that apply:
( ) Paranoid Personality Disorder (301.0)
( ) Schizotypal Personality Disorder (301.22)
( ) Borderline Personality Disorder (301.83)
( ) Narcissistic Personality Disorder (301.81)
( ) Dependent Personality Disorder (301.6)
( ) Schizoid Personality Disorder (301.20)
( ) Antisocial Personality Disorder (301.7)
( ) Histrionic Personality Disorder (301.50)

( ) Avoidant Personality Disorder (301.82)
( ) Obsessive-Compulsive Personality Disorder (301.4)

Axis III: General Medical Condition: [Obtained from PERSONAL DATA SHEET of Guide]

Has the person had a physical examination within the past year?

\_\_\_\_\_\_\_\_\_\_\_\_\_\_Yes \_\_\_\_\_\_\_\_\_\_\_\_\_\_No

If "No," encourage the person to have a complete physical examination.

Did the person list any medical problems?

\_\_\_\_\_\_\_\_\_\_\_\_\_\_Yes \_\_\_\_\_\_\_\_\_\_\_\_\_\_No.

If "Yes," is the person being followed by a physician?

\_\_\_\_\_\_\_\_\_\_\_\_\_\_Yes. \_\_\_\_\_\_\_\_\_\_\_\_\_\_No.

If "No", encourage the person to get a regular physician.

Is the person taking any current medications (including any prescription drugs, vitamins, herbs, or over-the-counter)?

\_\_\_\_\_\_\_\_\_\_\_\_\_\_Yes \_\_\_\_\_\_\_\_\_\_\_\_\_\_No.

Axis IV: Psychosocial and Environmental Problems {Obtain from PERSONAL DATA SHEET}

Did the person describe any psychosocial and/or environmental problems?

\_\_\_\_\_\_\_\_\_\_\_\_\_\_Yes \_\_\_\_\_\_\_\_\_\_\_\_\_\_No

Describe additional problems, if any:

Axis V: Overall Level of Functioning at Time of Evaluation Range from 1–100:

100=Superior functioning with no symptoms
75=Slight impairment due to minor symptoms
50=Serious symptoms (e.g., suicidal ideation, lengthy obsessional rituals)
25=Delusions or hallucinations and/or serious impairment of functioning
10=Persistent danger of suicide or homicide and/or inability to take care of essential needs.

Enter person's score (from PERSONAL DATA SHEET):\_\_\_\_\_\_\_\_

For healthcare provider:

Enter you overall estimate of the person's functioning:\_\_\_\_\_\_\_\_

I have not used the Patient Guide for Self-Assessment of Psychiatric Disorders as a substitute for a complete, personal evaluation, but rather, as its name implies, as a guide only.

_______________________________________

Signature of Healthcare Provider

_______________________________________

Date

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of facilitating diagnosis of a psychiatric disorder in a patient, the method comprising the steps of:
   (a) providing the patient with at least two sets of one or more questions relating to one or more symptoms of a plurality of psychiatric disorders in a format which facilitates recording the patient's answers to the questions;
   (b) directing the patient to answer a first set of one or more questions relating to one or more symptoms of a plurality of psychiatric disorders;
   (c) directing the patient to a case study describing a psychiatric disorder based on the patient's answers to the first set of one or more questions;
   (d) directing the patient to compare himself or herself to the case study;
   (e) directing the patient to answer a second set of one or more questions relating to one or more symptoms of the psychiatric disorder described in the case study, the second set of one or more questions having a set of answer choices wherein each answer choice within the set has a value assigned to it, the answer choices relating to a frequency at which the patient suffers the one or more symptoms of the psychiatric disorder described in the case study; and
   (f) establishing a preliminary disorder indication based on the values of the answer choices chosen by the patient to the second set of questions, whereby diagnosis of a psychiatric disorder in the patient is facilitated.

2. The method of claim 1, wherein the value assigned to each of the answer choices to the second set of questions each comprises a numerical value.

3. The method of claim 2, wherein the step of establishing a preliminary disorder indication based on the values of the answer choices chosen by the patient to the second set of questions further comprises:
   (a) summing the numerical values of the answer choices chosen by the patient to the second set of questions; and
   (b) establishing a preliminary disorder indication based on a sum of the values of the answer choices chosen by the patient to the second set of questions.

4. The method of claim 3, wherein the step of establishing a preliminary disorder indication based on a sum of the values of the answer choices chosen by the patient to the second set of questions further comprises providing a numerical range such that if the sum of the values of the answer choices chosen by the patient to the second set of questions falls within the numerical range, the sum is indicative of the preliminary disorder indication.

5. The method of claim 1, further comprising the step of directing the patient to provide details relating to any of the patient's answers.

6. The method of claim 5, further comprising directing the patient to provide details relating to the patient's comparison of himself or herself to the case study.

7. The method of claim 1, further comprising
   (a) directing the patient either to an additional case study or an additional set of questions, or to both, based the patient's answers to the first set of one or more questions, on the patient's comparison of himself or herself to the case study, or on the patient's answers to the second set of one or more questions, wherein the additional case study and the additional set of questions relate to an additional psychiatric disorder; and
   (b) establishing an additional preliminary disorder indication based on the answers or responses by the patient to the additional case study, the additional set of questions, or to both.

8. The method of claim 1, further comprising collecting general health information and other general identifying information from the patient.

9. The method of claim 1, wherein the psychiatric disorders are selected from a group consisting of major depressive disorder, dysthymia, manic episode, hypomanic episode, bipolar disorder, alcohol abuse, alcohol dependence, drug abuse, drug dependence, pre-menstrual syndrome, obsessive disorder, compulsive disorder, panic disorder, phobias, generalized anxiety disorder, eating disorder, acute stress disorder, post traumatic stress disorder, dissociative disorders, and combinations thereof.

10. The method of claim 1, wherein the sets of questions relating to the one or more symptoms of the plurality of psychiatric disorders track categories of psychiatric disorders presented in the *Diagnostic and Statistical Manual of Mental Disorders, Fourth Edition.*

11. The method of claim 1, further comprising summarizing and recording data generated by the steps of claim 1.

12. The method of claim 11, further comprising preparing a formal diagnosis based on the summarized and recorded data.

13. A method of facilitating diagnosis of a psychiatric disorder in a patient, the method comprising the steps of:
(a) providing the patient with one or more questions relating to symptoms of one or more psychiatric disorders in a format which facilitates recording the patient's answers to the one or more questions, wherein each of the one or more questions have a set of answer choices wherein each answer choice within the set has a numerical value assigned to it, the answer choices relating to a frequency at which the patient suffers the symptoms of a psychiatric disorder;
(b) summing the numerical values of the answer choices chosen by the patient to the one or more questions; and
(c) establishing a preliminary disorder indication based on a sum of the values of the answer choices chosen by the patient to the one or more questions,
whereby diagnosis of a psychiatric disorder in the patient is facilitated.

14. The method of claim 13, wherein the step of establishing a preliminary disorder indication based on a sum of the values of the answer choices chosen by the patient to the one or more questions further comprises providing a numerical range such that if the sum of the values of the answer choices chosen by the patient to the one or more questions falls within the numerical range, the sum is indicative of a particular preliminary disorder indication.

15. The method of claim 13, further comprising
(a) directing the patient either to an additional case study or an additional set of questions, or to both, based the patient's answers to the one or more questions, wherein the additional case study and the additional set of questions relate to an additional psychiatric disorder; and
(b) establishing an additional preliminary disorder indication based on the answers or responses by the patient to the the additional set of questions.

16. The method of claim 13, further comprising collecting general health information from the patient.

17. The method of claim 13, further comprising summarizing and recording data generated by the steps of claim 13.

18. The method of claim 17, further comprising preparing a formal diagnosis based on the summarized and recorded data.

19. The method of claim 13, wherein the psychiatric disorders are selected from the group consisting of major depressive disorder, dysthymia, manic episode, hypomanic episode, bipolar disorder, alcohol abuse, alcohol dependence, drug abuse, drug dependence, pre-menstrual syndrome, obsessive disorder, compulsive disorder, panic disorder, phobias, generalized anxiety disorder, eating disorder, acute stress disorder, post traumatic stress disorder, dissociative disorders, and combinations thereof.

20. The method of claim 13, wherein the one or more questions relating to one or more symptoms of one or more psychiatric disorders track categories of psychiatric disorders presented in the *Diagnostic and Statistical Manual of Mental Disorders, Fourth Edition.*

* * * * *